(12) United States Patent
Pelati et al.

(10) Patent No.: US 8,134,036 B2
(45) Date of Patent: Mar. 13, 2012

(54) PROCESS FOR LIQUID PHASE ALKYLATION

(75) Inventors: Joseph E. Pelati, Houston, TX (US); James R. Butler, League City, TX (US); Marcus Ledoux, Baton Rouge, LA (US)

(73) Assignee: Fina Technology Inc, Houston, TX (US)

( * ) Notice: Subject to any disclaimer, the term of this patent is extended or adjusted under 35 U.S.C. 154(b) by 125 days.

(21) Appl. No.: 12/047,873

(22) Filed: Mar. 13, 2008

(65) Prior Publication Data

US 2009/0234169 A1 Sep. 17, 2009

(51) Int. Cl.
*C07C 2/66* (2006.01)
*C07C 6/12* (2006.01)

(52) U.S. Cl. .................. 585/467; 585/475; 585/324

(58) Field of Classification Search .......... 585/467, 585/475, 324
See application file for complete search history.

(56) References Cited

U.S. PATENT DOCUMENTS

| | | | |
|---|---|---|---|
| 3,308,069 A | 3/1967 | Wadlinger et al. | |
| 4,185,040 A | 1/1980 | Ward et al. | |
| 4,642,226 A | 2/1987 | Calvert et al. | |
| 4,721,826 A | 1/1988 | Tiltscher et al. | |
| 4,870,222 A | 9/1989 | Bakas et al. | |
| 5,073,653 A | 12/1991 | Butler | |
| 5,081,323 A | 1/1992 | Innes et al. | |
| 5,145,817 A | 9/1992 | Sherrod | |
| 5,493,065 A | 2/1996 | Cheng et al. | |
| 5,907,073 A | 5/1999 | Ghosh | |
| 5,998,687 A | 12/1999 | Woodle et al. | |
| 6,376,729 B1 | 4/2002 | Merrill et al. | |
| 6,627,781 B1 | 9/2003 | Briot et al. | |
| 7,268,264 B2 | 9/2007 | Butler | |
| 7,268,542 B1 | 9/2007 | Wellstood et al. | |
| 2004/0138511 A1 | 7/2004 | Butler | |
| 2006/0084567 A1 | 4/2006 | Kelly et al. | |
| 2006/0194994 A1 | 8/2006 | Butler et al. | |
| 2007/0161836 A1 | 7/2007 | Butler et al. | |
| 2007/0179329 A1 | 8/2007 | Clark | |

OTHER PUBLICATIONS

Journal of Catalysis 205, 58-66 (2002); Xie et al.*
Indian Journal of Chemical Technology vol. 12, 2005; Thomas et al. Abstract only.*
J. Catal 205, 58-66 (2002).
Thomas et al. "Effect of rare earth metal ions on the structural and textural properties of NaFAU-Y zeolite and vapour phase alkylation of benzene with 1-octene" Indian Journal of Chemical Technology vol. 12, Nov. 2005, Abstract.
Zaiku et al. "Effect of Treatment with NaAIO2 Solution on the Surface Acid Properties of Zeolite Beta" Journal of Catalysis vol. 205, (2002), pp. 58-66.
Thomas et al. "Effect of rare earth metal ions on the structural and textural properties of NaFAU-Y zeolite and vapour phase alkylation of benzene with 1-octene" Indian Journal of Chemical Technology vol. 12, Nov. 2005.

* cited by examiner

*Primary Examiner* — Thuan Dinh Dang
(74) *Attorney, Agent, or Firm* — Bradley A. Misley

(57) ABSTRACT

A method for the liquid-phase alkylation of an aromatic substrate is disclosed. A reaction zone has at least one catalyst bed containing a first catalyst modified by the inclusion of a rare earth metal ion.

27 Claims, 2 Drawing Sheets

PROCESS FOR LIQUID PHASE ALKYLATION

BACKGROUND OF THE INVENTION

1. Field of the Invention

This invention relates generally to an alkylation process of aromatic compounds for the production of products such as ethylbenzene and styrene.

2. Description of the Related Art

Styrene is an important monomer used in the manufacture of many of today's plastics. Styrene is commonly produced by making ethylbenzene, which is then dehydrogenated to produce styrene. Ethylbenzene is typically formed by one or more aromatic conversion processes involving the alkylation of benzene in fixed bed or catalytic distillation processes.

Aromatic conversion processes utilizing a fixed bed catalyst are well known in the chemical processing industry. These reactions include the alkylation of aromatic compounds such as benzene to produce alkyl aromatics such as ethylbenzene and also the transalkylation of polyalkyl benzenes to monoalkyl benzenes. In general, such catalysts are selected from molecular sieve catalysts, such as zeolite Y or zeolite beta catalysts, for example.

For liquid phase alkylation processes the alkene fed to the reactor, for example ethylene, should be fully dissolved in the aromatic compound, for example benzene to minimize any deactivation of the liquid phase alkylation catalyst. Typically a large excess of aromatic compound is used to facilitate the dissolving of the alkene and minimize any gas phase alkenes. Any gas phase alkenes that are present can cause rapid deactivation of the typical liquid phase alkylation catalysts. A deactivated catalyst results in the need for regeneration or replacement of the catalyst, which can lead to a reduction in conversion, productivity, and efficiency of the system. In addition any operational upsets to the system can lead to gas phase alkene excursions in the reactor, which can also lead to accelerated catalyst deactivation. Upsets can reduce the run length of the catalyst, catalyst activity, and reduce the period of time between catalyst regeneration, further reducing conversion, productivity, and efficiency.

In view of the above, it would be desirable to have a process of producing alkyl aromatics, such as ethylbenzene, by liquid phase alkylation which is more resistant to any gas phase alkenes that may be present.

SUMMARY

The present invention discloses a method for the liquid-phase alkylation of an aromatic substrate by providing an alkylation reaction zone having one or more catalyst beds. At least one catalyst bed contains a first catalyst modified by the inclusion of a rare earth metal ion. A feedstock of an aromatic substrate and an alkylating agent are introduced into the alkylation reaction zone. The alkylation reaction zone is operated at temperature and pressure conditions such that the aromatic substrate is in a liquid phase to cause liquid-phase alkylation of the aromatic substrate to produce an alkylation product that is then withdrawn from the alkylation reaction zone.

The aromatic substrate can be benzene and the alkylating agent can be an ethylating or propylating agent, for example ethylene. The at least one catalyst bed containing the first catalyst can be located to contact the alkylating agent prior to any other catalyst that may be present. The rare earth metal ion can be cerium and can have a cerium content within the range of about 0.01 wt % to 5.0 wt %. The first catalyst can be a cerium modified zeolite catalyst and can be a cerium modified zeolite beta catalyst. The one or more catalyst beds can further contain a second catalyst having rare earth metal ion content less than the first catalyst, the second catalyst being located within the catalyst beds to contact the alkylating agent after the alkylating agent contacts the first catalyst. The first catalyst can have a greater resistance to gas phase ethylene than the second catalyst. The catalyst bed can comprise a split load of catalyst wherein the first catalyst contacts a feed stream of alkylating agent prior to the alkylating agent contacting the second catalyst. The feedstock can have a benzene: ethylene weight ratio per catalyst bed within the range of 1:1 to 100:1. Alternatively the feedstock can have a benzene: ethylene weight ratio per catalyst bed within the range of 2:1 to 75:1 or within the range of 5:1 to 20:1, with the minimum limit set by the ability of the reactor to control the temperature of the exothermic reaction. The aromatic substrate can comprise benzene and the alkylating agent can comprise ethylene and the ethylene can be provided from a dilute ethylene stream having less than 95% ethane content. Alternate embodiments can utilize a dilute ethylene stream having less than 90% ethane content, or less than 85% ethane content, or less than 80% ethane content, or between 20% to 80% ethane content.

The alkylation product can be supplied to an intermediate recovery zone for the separation and recovery of ethylbenzene and polyalkylated aromatic components, with at least a portion of the polyalkylated aromatic component being supplied to a transalkylation reaction zone. Benzene can be supplied to the transalkylation reaction zone, which is operated under temperature and pressure conditions to cause disproportionation of the polyalkylated aromatic fraction to produce a product having an enhanced ethylbenzene content and a reduced polyalkylated aromatic components content. The transalkylation zone can contain a transalkylation catalyst and be operated under temperature and pressure conditions to maintain the feedstock in the transalkylation zone in the liquid phase. The first catalyst that is modified by the inclusion of a rare earth metal ion can also be used as the transalkylation catalyst.

Yet another embodiment is a method for the liquid-phase alkylation of benzene involving a multi-stage alkylation reaction zone having a plurality of series-connected catalyst beds, at least one catalyst bed containing a first alkylation catalyst that is a cerium modified zeolite with elevated resistance to gas phase ethylene than the non-modified catalyst. The feedstock can have a benzene:ethylene weight ratio per catalyst bed within the range of 1:1 to 100:1. Alternatively the feedstock can have a benzene:ethylene weight ratio per catalyst bed within the range of 2:1 to 75:1 or within the range of 5:1 to 20:1. The ethylene can be provided from a dilute ethylene stream having less than 95% ethane content. Alternate embodiments can utilize a dilute ethylene stream having less than 90% ethane content, or less than 85% ethane content, or less than 80% ethane content, or between 20% to 80% ethane content. The alkylation multistage reaction zone is operated at temperature and pressure conditions in which the benzene is in a liquid phase to cause liquid-phase alkylation of the benzene in the presence of the alkylation catalysts to produce an alkylation product comprising ethylbenzene and one or more polyalkylated aromatic components. The alkylation product is removed from the multistage alkylation reaction zone and suppled to a recovery zone for the separation and recovery of ethylbenzene from the alkylation product and for the separation and recovery of polyalkylated aromatic components. The catalyst bed can contain a second alkylation catalyst, wherein the first alkylation catalyst has greater resistance to gas phase ethylene than the second alkylation catalyst, and any feedstock of ethylene contacts the first alkylation catalyst prior to contacting the second alkylation catalyst. The multistage alkylation reaction zone can have between 2 to 10 catalyst beds. The first alkylation catalyst can be a cerium modified zeolite catalyst. The first catalyst can have a cerium content within the range of about 0.01 wt % to 5.0 wt %.

At least a portion of the polyalkylated aromatic component and benzene can be supplied to a transalkylation reaction zone that is operated under temperature and pressure conditions to cause disproportionation of the polyalkylated aromatic component to produce a product having an enhanced ethylbenzene content and a reduced polyalkylated aromatic component content. The transalkylation zone can contain a transalkylation catalyst and be operated under temperature and pressure conditions effective to maintain the feedstock in the transalkylation zone in the liquid phase. The transalkylation catalyst can also be a cerium modified zeolite.

DETAILED DESCRIPTION

Figure 1:
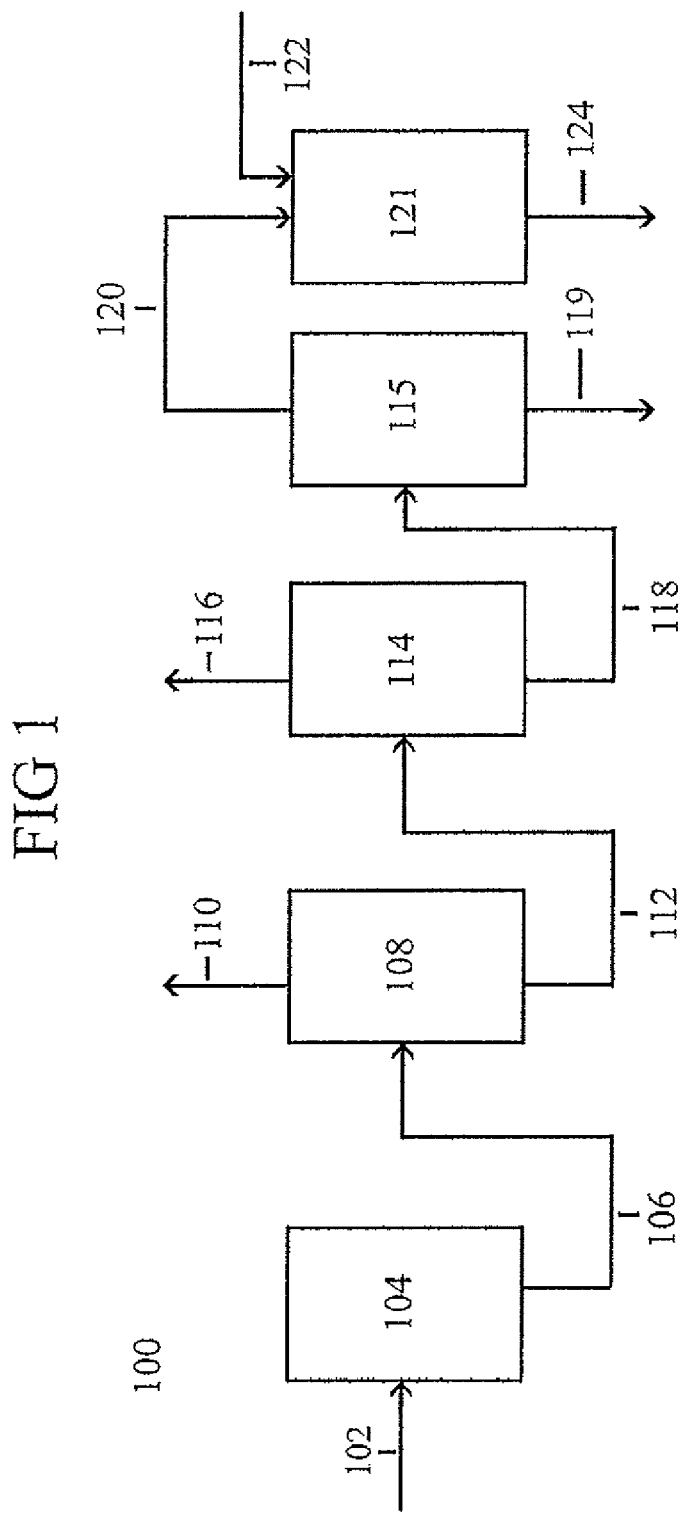
FIG. 1 is a schematic block diagram illustrating a process for making ethylbenzene.

Embodiments of the present invention can be is used for the alkylation of benzene and other aromatic feedstreams with ethylene, propylene and other light alkene feedstreams. Typically, an alkylation reactor will produce a mixture of monoalkyl and polyalkyl benzenes and will be operated in conjunction with a transalkylation reactor. There are typically separation stages between the alkylation and transalkylation reaction stages for the separation and recovery of ethylbenzene from the alkylation product and for the separation and recovery of polyalkylated aromatic components. At least a portion of the polyalkylated aromatic component can be supplied to a transalkylation reaction zone. Benzene is supplied to the transalkylation reaction zone and the transalkylation reaction zone is operated under temperature and pressure conditions to cause disproportionation of the polyalkylated aromatic fraction to produce an enhanced ethylbenzene content and a reduced polyalkylated content. To effect the transalkylation reaction, the transalkylation zone may contain a molecular sieve catalyst and be operated under temperature and pressure conditions effective to maintain the feedstock in the transalkylation zone in the liquid phase. Ethylbenzene can then be sent to a dehydrogenation process to produce styrene.

Liquid phase alkylation of benzene with alkenes can be practiced using known catalysts. Zeolites and shape selective silica-alumina catalysts are generally used. The liquid phase process is run at temperature and pressure conditions effective to maintain the feedstock in the alkylation zone in the liquid phase. One aspect for this liquid phase process is the selection of reactor conditions so that the alkene fed to the reactor is fully dissolved in the benzene. This is usually done by adjusting the pressure and the benzene/alkene ratio where the alkene is the limiting reagent. Typically a large excess of benzene is used to facilitate the dissolving of the alkene and minimize any gas phase alkenes. Any gas phase alkenes that are present can cause rapid deactivation of the typical liquid phase alkylation catalysts. A deactivated catalyst results in the need for regeneration or replacement of the catalyst, which can lead to a reduction in conversion, productivity and efficiency of the system. Any unplanned upsets to the system can lead to gas phase alkene excursions in the reactor, which can lead to accelerated catalyst deactivation. Upsets can reduce the run length of the catalyst, catalyst activity and reduce the period of time between catalyst regeneration, further reducing conversion, productivity and efficiency.

While a high purity alkene may be desired for the alkylating agent feedstock in liquid phase alkylation reactions, they can also occur with relatively dilute alkene feeds. In the alkylation of benzene with ethylene using fixed bed catalysts, ethylene with a purity as low as about 20 mol % can be used. In one embodiment the ethylene can range from 100% to 20% in the alkene feed. In an alternate embodiment the ethylene can range from 95% to 20% in the alkene feed. In an alternate embodiment the ethylene can range from 90% to 20% in the alkene feed. In an alternate embodiment the ethylene can range from 85% to 20% in the alkene feed. Typically the remaining alkylating agent feedstock will be predominantly ethane. The present invention can be beneficial in liquid phase alkylation reactions utilizing relatively dilute alkene feeds.

One embodiment of the present invention can involve the use of a multi-stage alkylation reactor having a plurality of series-connected catalyst beds filled with alkylation catalysts. One or more of the catalyst beds contains an alkylation catalyst having a higher resistance to gas-phase alkenes, hereinafter referred to as the "more resistant catalyst". In addition, one or more catalyst beds of the alkylation reactor can contain an alkylation catalyst having a lower resistance to gas-phase alkenes referred to as the "less resistant catalyst". The less resistant catalyst will be located downstream of the more resistant catalyst where the chances of encountering gas-phase alkenes are minimized.

The actual location of the catalyst may vary depending whether the reactor is a top feed, bottom feed, or horizontal reactor. In the examples given herein, the reactors used are bottom feed reactors, with the more resistant catalyst located in the lower portion of the bed, and the less resistant catalyst located in the upper portion. In a typical liquid-phase alkylation reactor, there may be between 2 to 10 catalyst beds in the reactor, for example. In one embodiment there is a greater proportion of the less resistant catalyst used within the reaction zone as opposed to the less resistant catalyst. Thus in an one embodiment, only one or two beds of a multi-bed reactor system may be filled with the more resistant catalyst, with the remaining beds being filled with one or more beds of a less resistant catalyst if there is no addition of alkenes at locations between the respective beds. Alternately, when there is addition of alkenes at locations between the respective beds, each bed may have a bottom layer of the more resistant catalyst with the top layer of each bed being the less resistant catalyst. The multi-bed reactor system can comprise a single reactor with multiple beds or can instead comprise a plurality of reactors, each having one or more beds. The catalyst beds can be separated by actual or functional barriers known in the art, such as by the placement of an inert material between the catalyst layers. Alternately, the catalyst beds can be located adjacent to each other. For example in a bottom feed reactor, the more resistant catalyst can be loaded first and the less resistant catalyst loaded second on top of the more resistant catalyst, thereby the more resistant catalyst would contact the reactants before the less resistant catalyst. In another embodiment whereby the catalysts are adjacent to each other, there can be mixing of the two catalysts to some degree at the interface of the two beds.

In one embodiment the less resistant catalyst can have a high activity, but tend to deactivate more rapidly in the presence of gas phase alkenes than the more resistant catalyst. The more resistant catalyst used in the initial stage can react with any gas phase alkenes present in the feed. The more resistant catalyst can react with the gas phase alkenes to an extent to reduce or eliminate the quantity of gas phase alkenes present prior to contact with the less resistant catalyst. This lowering of the quantity of gas phase alkenes present upon contact with the less resistant catalyst can extend the useful life of the less resistant catalyst and reduce the frequency of catalyst regeneration or replacement. The use of the more resistant catalyst in the initial stages of the reaction can reduce the need that the alkene fed to the reactor be fully dissolved in the benzene. The benzene/alkene constraint that requires a fully dissolved alkenecan be eliminated because the more resistant catalyst used in the initial stages can react with sufficient alkenes to eliminate the gas phase alkene prior to reaching the less resistant catalyst layer. Therefore a large excess of benzene to facilitate the complete dissolving of the alkene and minimize any gas phase alkenes is not needed. Wherein the typical benzene:alkene weight ratio per catalyst bed can vary from 1:1 to 100:1; in one embodiment the per catalyst bed ratio can range from 15:1 to 70:1; and in alternate embodiments the per catalyst bed ratio can range from 2:1 to 75:1; or from 5:1 to 50:1; or from 5:1 to 20:1; or from about 10:1 to 25:1.

Without the need for a large excess of benzene, the benzene/alkene ratio can be adjusted based on conversion, productivity or efficiency considerations rather than alkene solubility alone. More alkylation product can be produced per reactor than when the dissolved alkene constraint is in effect for a given benzene flow rate. Reliability can be improved because any gas phase alkene present due to unplanned upsets in the reactor can be removed by the reactions of the more resistant catalyst, without causing accelerated deactivation of the less resistant catalysts. Improved reliability can lead to improved productivity when the period of time between catalyst regeneration is extended and run length increased. Therefore this multi-catalyst system can have advantages in conversion, productivity and reliability.

The less resistant catalyst can have an activity that is the same, higher or lower than the more resistant catalyst. The less resistant catalyst can also have other factors that are the same, higher or lower than the more resistant catalyst, such as cost, durability, ease of regeneration and the like, that can be considered when determining the design of the overall catalyst system.

One embodiment of the invention is a system involving a multistage alkylation reactor with a split load of catalyst with the output of the reactor coupled to a separation system, which in turn supplies a polyethylbenzene feed to a transalkylation reactor. The separation system can be a multi-stage separation system, for example a four-stage separation system. One or more parallel alkylation and transalkylation reactors can be employed. The parallel alkylation reactors can be simultaneously operated in an alkylation mode while periodically one reactor can be taken off-stream with the feed completely supplied to the remaining on-stream reactor or reactors. In one embodiment illustrated and described below, two parallel reactors are employed, although three or more reactors can also be employed in parallel. A similar configuration can be employed for the transalkylation reactors. The result is that simultaneous catalyst regeneration can occur in one reactor which is taken off-stream, during continued operation of the remaining alkylation and/or transalkylation reactors. In the case where two parallel reactors are used, it can be seen that this mode of operation can, for the same flow rate of feed, result in the operation of the reactors at two different space velocities, during regeneration of one reactor, the space velocity of the remaining on-stream reactor may be about twice that of when both parallel reactors are in operation.

The alkylation reaction may be carried out with benzene in the gas phase, the liquid phase, or the supercritical phase. Generally the invention will be carried out under conditions to effect alkylation of the benzene, or other aromatic substrate, in the liquid phase or supercritical phase. Molecular sieve catalysts, such as a conventional or modified zeolite catalyst, are generally employed. The molecular sieve catalyst employed in the alkylation reaction zone and the transalkylation reaction zone may be the same or different, but typically different molecular sieves will be employed.

In one embodiment of the invention, parallel alkylation and transalkylation reactors can be employed. This results in a mode of operation in which the parallel alkylation reactors can be simultaneously operated in an alkylation mode while periodically one reactor can be taken off-stream with the feedstream completely supplied to the on-stream reactor. In the embodiment described below two parallel reactors are employed, although it is to be recognized that three or more reactors can likewise be employed in parallel. A similar configuration can be employed for the transalkylation reactors. The result is that simultaneous catalyst regeneration or other maintenance operations can occur in one reactor during operation of the remaining alkylation and/or transalkylation reactors. Assuming that two parallel reactors are employed, it can be seen that this mode of operation will, for the same flow rate of feedstream, result in the operation of the reactors at two different space velocities, with the space velocity during regeneration or maintenance of a reactor being about twice that when both parallel reactors are in operation.

Liquid Phase Alkylation With liquid phase alkylation the reaction zone is operated at such temperature and pressure to maintain essentially liquid phase conditions. For the production of ethylbenzene, the reaction temperature may range from about 40° C. to 320° C., and is generally between about 120° C. and 280° C. In one embodiment a reaction temperature between about 190° C. and 240° C. can be used. The alkylation pressure is generally kept high enough to ensure a liquid phase. In one embodiment the pressures can range from 300 psig to 1600 psig, in an alternate embodiment the pressures can range from 500 psig to 800 psig. When operating under essentially liquid phase conditions, generally an up-flow reactor mode will be employed. Flow rates typically can range from liquid hourly space velocity (LHSV) between about 1 and 100 $hr^{-1}$ per bed and an aromatic substrate:alkylating agent molar ratio between about 1:1 and 100:1. In one embodiment LHSV's between about 10 to 70 $hr^{-1}$ per bed and aromatic substrate:alkylating agent molar ratios between about 2:1 to 50:1 are used. In another embodiment LHSV's between about 10 to 70 $hr^{-1}$ per bed and aromatic substrate:alkylating agent molar ratios between about 5:1 to 20:1 are used.

Critical Phase Alkylation The alkylation reactions can be operated under supercritical conditions, that is, pressure and temperature conditions which are above the critical pressure and critical temperature of benzene. Specifically, the temperature in the alkylation zone is at or above 280° C., and the pressure is at or above 550 psig. Preferably, the temperature in the alkylation reactor will be maintained at an average value within the range of 290° C. to 350° C. and a pressure within the range of 550 psig to 1600 psig and in some embodiments from 550 psig to 850 psig. The critical phase alkylation reaction is exothermic with a positive temperature gradient from the inlet to the outlet of the reactor, typically providing a temperature increment increase within the range of about 20 to 40° C. The operation of the alkylation reaction zone in the supercritical region enables the alkylation zone to be operated under conditions in which the benzene:ethylene mole ratio can be maintained at relatively low levels, usually somewhat lower than the benzene:ethylene mole ratio encountered when the alkylation reaction zone is operated under liquid phase conditions. In most cases, the benzene:ethylene mole ratio will be within the range of 1:1 to 15:1. In some instances, the benzene:ethylene mole ratio will be maintained during at least part of a cycle of operation at a level within the lower end of this range, specifically, at a benzene:ethylene mole ratio of less than 10:1. A benzene:ethylene mole ratio within the range of 3:1 to 8:1 may be employed.

Operation in the supercritical phase offers the advantages of gas phase alkylation in which the benzene:ethylene ratio can be kept low but without the problems associated with by-product formation, specifically xylene formation, often encountered in gas-phase alkylation. At the same time, operation in the supercritical phase offers the advantages accruing to liquid phase alkylation in which the by-product yield can be controlled to low levels. The pressures required for operation in the supercritical phase are not substantially greater than those required in liquid phase alkylation, and the benzene in the supercritical phase functions as a solvent to keep the molecular sieve catalyst clean and to retard coking leading to deactivation of the catalyst. The alkylation reaction zone can be operated under supercritical conditions and at a feed rate to provide a space velocity enhancing diethylbenzene production while retarding by-products production. In one embodiment the space velocity of the benzene feed stream will be within the range of 10 to 150 hr$^{-1}$ LHSV per bed, and in some embodiments from 40 to 100 hr$^{-1}$ LHSV per bed.

Liquid Phase Transalkylation The transalkylation reactor is operated under conditions to maintain the benzene and alkylated benzenes within the transalkylation reactor in the liquid phase. Typically, the transalkylation reactor may be operated to provide an average temperature within the transalkylation reactor of from about 65° C. to 300° C. and an average pressure of about 300 psig to about 1200 psig. In one embodiment the pressures can range from 500 psig to 800 psig, in an alternate embodiment the pressures can range from 550 psig to 650 psig. The weight ratio of benzene:polyethylbenzene will generally be at least 1:1 and in some embodiments will be within the range of 1:1 to 10:1 and in alternate embodiments will range from 1:1 to 5:1.

In one embodiment of a multi-stage reaction zone of the present invention, a benzene-ethylene mixture is introduced to the first catalyst bed at the initial stage of the reaction zone and also in between the several successive stages of catalyst beds. In the examples presented, ethylene can be supplied along with benzene to the first catalyst bed located at the top or upper end of the reactor. In addition, interstage injection of ethylene and/or benzene can be added between the subsequent catalyst beds. The alkylation reactor may be operated with the benzene to ethylene weight ratio remaining steady, increasing or decreasing along the length of the reactor because of the interstage injection of ethylene and the subsequent alkylation of the benzene to ethylbenzene and polyethylbenzenes. With a split-load of catalyst such that at each catalyst bed the reactants first contact the more resistant catalyst, any gas phase ethylene will be reacted by the more resistant catalyst prior to any contact of a less resistant catalyst, thereby reducing the occurrence of less resistant catalyst deactivation. Due to increased efficiencies of the split-load catalyst reactor, the alkylation feedstock may have a much lower benzene-to-ethylene weight ratio than if only a single catalyst were used.

FIG. 1 illustrates a schematic block diagram of an embodiment of a liquid phase alkylation process 100. The process 100 generally includes supplying an input stream 102 (e.g., a first input stream) to an alkylation system 104 (e.g., a first alkylation system.) The alkylation system 104 is generally adapted to contact the input stream 102 with an alkylation catalyst to form an alkylation output stream 106 (e.g., a first output stream). In one embodiment the input stream 102 can include benzene and ethylene and the alkylation output stream 106 can include ethylbenzene. At least a portion of the alkylation output stream 106 passes to a first separation system 108. An overhead fraction is generally recovered from the first separation system 108 via line 110 while at least a portion of the bottoms fraction is passed via line 112 to a second separation system 114.

An overhead fraction is generally recovered from the second separation system 114 via line 116 while at least a portion of a bottoms fraction is passed via line 118 to a third separation system 115. A bottoms fraction is generally recovered from the third separation system 115 via line 119 while at least a portion of an overhead fraction is passed via line 120 to a transalkylation system 121. In addition to the overhead fraction 120, an additional input, such as additional aromatic compound, is generally supplied to the transalkylation system 121 via line 122 and contacts the transalkyation catalyst, forming a transalkylation output 124.

The process 100 may be modified based on unit optimization. Additional process equipment, such as heat exchangers, may be employed within the processes described herein and such placement is generally known to one skilled in the art. Further, while described below in terms of primary components, the streams indicated below may include any additional components as known to one skilled in the art.

The input stream 102 generally includes an aromatic compound and an alkylating agent. The aromatic compound may include for example benzene, toluene, xylene or naphthalene.

The alkylating agent may include olefins (e.g., ethylene, propylene, butene and pentene), alcohols (e.g., methanol, ethanol, propanol, butanol and pentanol), aldehydes (e.g., formaldehyde, acetaldehyde, propionaldehyde, butyraldehyde and n-valeraldehyde) and/or alkyl halides (e.g., methyl chloride, ethyl chloride, propyl chloride, butyl chloride, and pentyl chloride), for example. In one embodiment, the alkylating agent includes a mixture of light olefins, such as mixtures of ethylene, propylene, butene and/or pentenes, for example.

In one embodiment, the alkylation system 104 may include a plurality of multi-stage reaction vessels (not shown). In one embodiment, the plurality of multi-stage reaction vessels include a plurality of catalyst beds, such beds containing an alkylation catalyst (not shown.) Such reaction vessels are liquid phase reactors typically operated at reactor temperatures and pressures sufficient to maintain the alkylation reaction in the liquid phase. Such temperatures and pressures are generally determined by individual process parameters. Although the conditions are such to maintain the alkylation reaction in the liquid phase, in some instances a portion of the alkylating agent may remain in the gas phase, for example in a benzene/ethylene alkylation reaction a portion of the ethylene may remain in the gas phase. In other instances a plant upset may alter the process parameters in a way that would allow a portion of the ethylene or other alkene present to come out of solution from the aromatic compound and be present in a gas phase. In a specific embodiment, benzene is recovered through line 110 and recycled (not shown) as input to the alkylation system 104, while ethylbenzene and/or polyalkylated benzenes are recovered via line 112.

The alkylation output 106 generally includes a second aromatic compound. In one embodiment, the second aromatic compound includes ethylbenzene, for example. The first separation system 108 may include any process or combination of processes known to one skilled in the art for the separation of aromatic compounds. For example, the first separation system 108 may include one or more distillation columns (not shown,) either in series or in parallel. The number of such columns may depend on the volume of the alkylation output 106.

The overhead fraction 110 from the first separation system 108 generally includes the first aromatic compound, such as benzene, for example. The first aromatic compound can be recycled to the alkylation system 104 (not shown) and/or can be supplied to the transalkylation system 121 (not shown). The bottoms fraction 112 from the first separation system 108 generally includes the second aromatic compound, such as ethylbenzene, for example.

The second separation system 114 may include any process known to one skilled in the art, for example, one or more distillation columns (not shown), either in series or in parallel. The overhead fraction 116 from the second separation system 114 generally includes the second aromatic compound, such as ethylbenzene, which may be recovered and used for any suitable purpose, such as the production of styrene, for example. The bottoms fraction 118 from the second separation system 114 generally includes heavier aromatic compounds, such as polyethylbenzene, for example.

The third separation system 115 generally includes any process known to one skilled in the art, for example, one or more distillation columns (not shown), either in series or in parallel. In a specific embodiment, the overhead fraction 120 from the third separation system 115 may include polyethylbenzene, for example, which can be sent to a transalkylation system 121. The bottoms fraction 119 (e.g., heavies) may be recovered from the third separation system 115 for further processing and recovery (not shown).

The transalkylation system 121 generally includes one or more reaction vessels having a transalkylation catalyst disposed therein. The transalkylation reaction vessels may include any reaction vessel, combination of reaction vessels and/or number of reaction vessels (either in parallel or in series) known to one skilled in the art. In one embodiment, the transalkylation system 121 is operated under liquid phase conditions. The transalkylation output 124 generally includes the second aromatic compound, such as ethylbenzene, for example. The transalkylation output 124 can be sent to the second separation system 114 for separation and recovery of the second aromatic compound, such as ethylbenzene.

In a specific embodiment, the input stream 102 includes benzene and ethylene. The benzene may be supplied from a variety of sources, such as a fresh benzene source and/or a variety of recycle sources.

As previously discussed, the alkylation system 104 generally includes an alkylation catalyst. The input stream 102, e.g., benzene/ethylene, contacts the alkylation catalyst during the alkylation reaction to form the alkylation output 106, e.g., ethylbenzene. Unfortunately, alkylation catalyst systems generally experience deactivation requiring either regeneration or replacement. The deactivation results from a number of factors. One of those factors is that any gas phase alkenes present in the input stream 102 can reduce the activity of the alkylation catalyst.

In one embodiment the alkylation system 104 can have multiple reactors (not shown), one or more of the reactors can utilize the more resistant catalyst. The reactors containing the more resistant catalyst will typically be located to contact the reactants where any gas phase alkenes may be present, such as where alkenes are added to the alkylation system 104. In addition, one or more of the reactors can contain the less resistant catalyst where gas phase alkenes will not be present, such as down stream from the more resistant catalyst.

One embodiment of the present invention can involve the use of a multi-stage alkylation reactor having a plurality of series-connected catalyst beds filled with the alkylation catalysts. One or more of the catalyst beds can be filled with the more resistant catalyst. The bed or beds containing the more resistant catalyst will typically be located to contact the input stream 102 first, where the gas phase alkenes are likely to be present. In addition, one or more catalyst beds of the alkylation reactor can contain the less resistant catalyst. The less resistant catalyst will typically be located down stream from the more resistant catalyst, where gas phase alkenes are not likely to be present.

Figure 2:
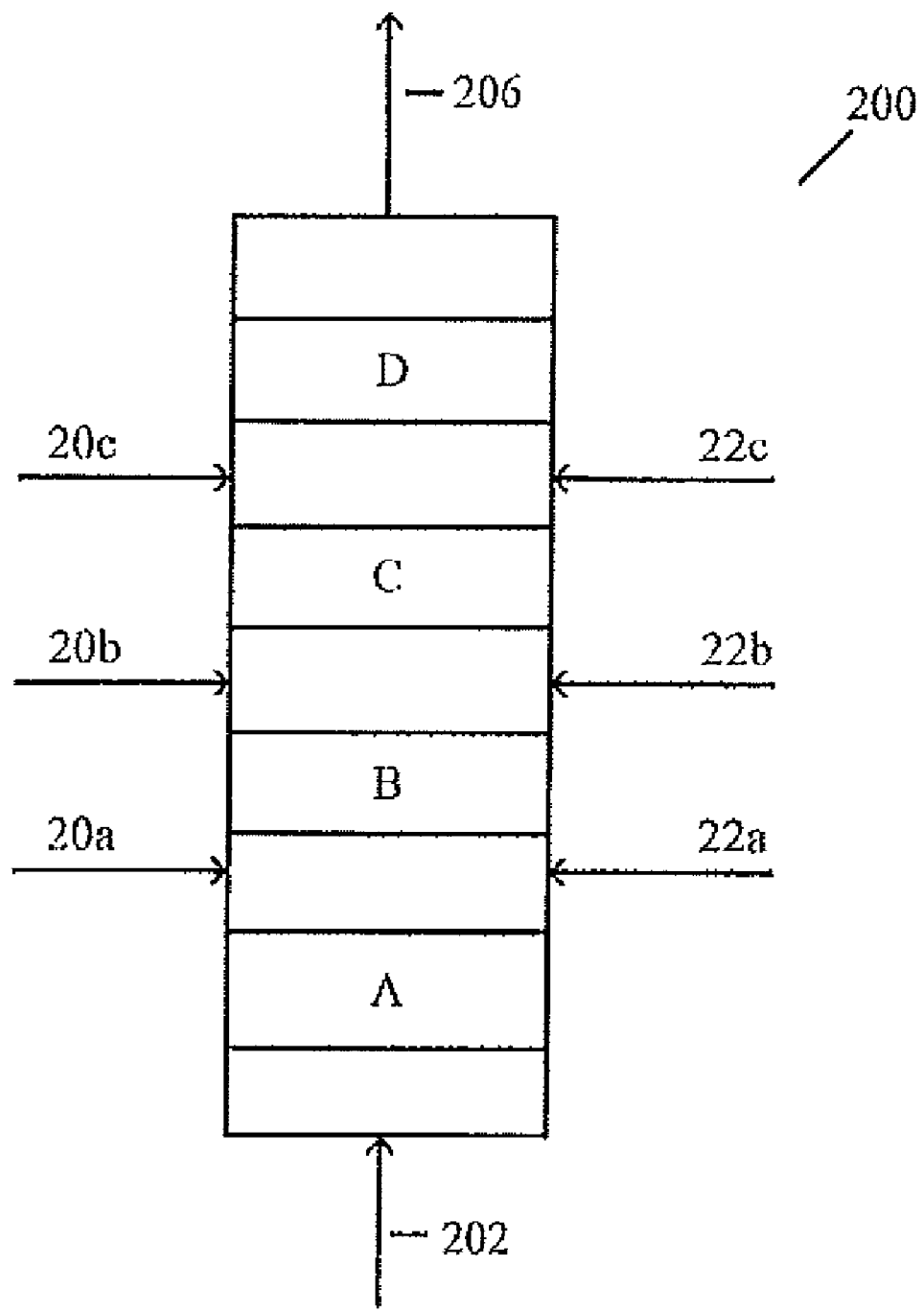
FIG. 2 is an illustration of a multi-stage alkylation reactor having series-connected catalyst beds filled with alkylation catalysts according to an embodiment of the present invention.

One embodiment of an alkylation system with multiple beds is illustrated in FIG. 2. The reactor 200 comprises four series connected catalyst beds designated as beds A, B, C and D. The input stream 202, e.g., benzene/ethylene, enters the bottom of the reactor 200 and comes in contact with catalyst beds A, B, C and D in sequence. An ethylene feed stream can also be supplied via lines 20a, 20b and 20c to provide for interstage injection of ethylene. Benzene can also be supplied between the catalyst stages via secondary benzene supply lines 22a, 22b and 22c, respectively. The alkylation output stream 206 exits the reactor 200 to proceed to a separation system for further processing. Each of the catalyst beds can be entirely filled with the more resistant catalyst, can have a split load of more resistant catalyst and less resistant catalyst, or can be entirely filled with the less resistant catalyst. Which beds utilize the more resistant catalyst may be at least partially determined by the operating conditions. The quantities of interstage injection of ethylene and benzene, for example, can determine which of the catalyst beds will have a high probability of contacting gas phase ethylene. For example, if a high quantity of ethylene is to be injected via line 20b, in relation to the composition within the reactor at that point and to the quantity of benzene to be injected via line 22b, the possibility that bed C may come in contact with gas phase ethylene may increase and therefore the need for the more resistant catalyst may increase. In one embodiment there can be interstage injection of ethylene prior to each catalyst bed and each of the beds can contain at least some of the more resistant catalyst which will contact the reactants prior to any contact of the less resistant catalyst.

Embodiments of the invention can utilize a cerium modified zeolite catalyst as the more resistant catalyst. Unexpectedly, it has been found that a cerium modified zeolite catalyst can be have a higher resistance to gas phase alkene deactivation than that of previous zeolite catalysts. In alternate embodiments the other alkylation and/or transalkylation catalysts may also utilize such a cerium modified catalyst. In one embodiment both the more resistant and the less resistant catalysts can comprise one or more cerium modified catalyst. In embodiments where dilute ethylene is used or ethylene purity is less than about 80%, it can be desirable that all of the catalysts used be a cerium modified zeolite catalyst. In an alternate embodiment the ethylene can range from 95% to 20% in the alkene feed and all of the alkylation catalyst is a cerium modified zeolite catalyst. In an alternate embodiment the ethylene can range from 90% to 20% in the alkene feed and all of the alkylation catalyst is a cerium modified zeolite catalyst. In an alternate embodiment the ethylene can range from 85% to 20% in the alkene feed and all of the alkylation catalyst is a cerium modified zeolite catalyst.

In one embodiment, the cerium modified zeolite catalyst (e.g., cerium beta) is a cerium modified zeolite beta catalyst. In an aspect, the cerium beta catalyst includes the cerium beta catalyst has been developed by Total Petrochemicals that has been unexpectedly found to have a higher resistance to gas phase alkene deactivation than that of previous zeolite catalysts, which is further described in U.S. Pat. Application Publication No. 2007/0161836, and is fully incorporated by reference herein. In one embodiment the cerium modified zeolite beta catalyst is used within a liquid phase or critical phase alkylation reaction.

The cerium modified zeolite beta catalyst may be formed from any zeolite catalyst known to one skilled in the art. For example, the cerium beta catalyst may include zeolite beta modified by the inclusion of cerium. Any method of modifying the zeolite beta catalyst with cerium may be used. For example, in one embodiment, the zeolite beta may be formed by mildly agitating a reaction mixture including an alkyl metal halide and an organic templating agent for a time sufficient to crystallize the reaction mixture and form the zeolite beta (e.g., from about 1 day to many months via hydrothermal digestion), for example. The alkyl metal halide may include silica, alumina, sodium or another alkyl metal oxide, for example. The hydrothermal digestion may occur at temperatures of from slightly below the boiling point of water at atmospheric pressure to about 170° C. at pressures equal to or greater than the vapor pressure of water at the temperature involved, for example.

The zeolite beta may have a silica to alumina molar ratio (expressed as SiO2/Al2O3) of from about 10 to about 200 or about 20 to about 50, for example. In one embodiment, the zeolite beta may have a low sodium content, e.g., less than about 0.2 wt. % expressed as Na2O, or less than about 0.02 wt. %, for example. The sodium content may be reduced by any method known to one skilled in the art, such as through ion exchange, for example. The formation of zeolite beta is further described in U.S. Pat. Nos. 3,308,069 and 4,642,226, which are incorporated by reference herein.

In another embodiment, it is contemplated that a cerium promoted zeolite Y catalyst may be used. It is further contemplated that the zeolite Y catalyst may be modified with cerium in the same manner as the modification of zeolite beta. The formation of Zeolite Y is described in U.S. Pat. No. 4,185,040, which is incorporated by reference herein. In one embodiment the cerium modified zeolite Y catalyst is used within a liquid phase transalkylation reaction.

In one embodiment, the zeolite catalyst is modified with a rare earth metal ion, such as lanthanum, cerium, neodymium, or praseodymium, for example. As previously discussed, it has been discovered that cerium based zeolite catalyst demonstrate an unexpected improvement in resistance to gas phase alkene degradation over other zeolite catalyst systems. However, it is contemplated that the acidity of the rare earth metal ion based zeolite catalyst systems may be modified to enhance the resistance to gas phase alkene degradation. Such modification of the acidity may be accomplished, for example, through the processes described in J. Catal. 205, 58-66 (2002), which is incorporated by reference herein.

When regeneration of any catalyst within the system is desired, the regeneration procedure generally includes processing the deactivated catalyst at high temperatures, although the regeneration may include any regeneration procedure known to one skilled in the art. Once a reactor is taken off-line, the catalyst disposed therein may be purged. Off-stream reactor purging may be performed by contacting the catalyst in the off-line reactor with a purging stream, which may include any suitable inert gas (e.g., nitrogen), for example. The off-stream reactor purging conditions are generally determined by individual process parameters and are generally known to one skilled in the art.

The catalyst may then undergo regeneration. The regeneration conditions may be any conditions that are effective for at least partially reactivating the catalyst and are generally known to one skilled in the art. For example, regeneration may include heating the alkylation catalyst to a temperature or a series of temperatures, such as a regeneration temperature of from about 50° C. to about 400° C. above the purging or alkylation reaction temperature, for example. Upon catalyst regeneration, the reactor with its regenerated catalyst is then typically ready to be placed on-line for continued production.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

The term "activity" refers to the weight of product produced per weight of the catalyst used in a process per hour of reaction at a standard set of conditions (e.g., grams product/gram catalyst/hr).

The term "conversion" refers to the percentage of input converted.

The term "deactivated catalyst" refers to a catalyst that has lost enough catalyst activity to no longer be efficient in a specified process.

The term "recycle" refers to returning an output of a system as input to either that same system or another system within a process. The output may be recycled to the system in any manner known to one skilled in the art, for example, by combining the output with the input stream or by directly feeding the output into the system. In addition, multiple input streams may be fed to a system in any manner known to one skilled in the art.

The term "regenerated catalyst" refers to a catalyst that has regained enough activity to be efficient in a specified process. Such efficiency is determined by individual process parameters.

The term "regeneration" refers to a process for renewing catalyst activity and/or making a catalyst reusable after its activity has reached an unacceptable level. Examples of such regeneration may include passing steam over a catalyst bed or burning off carbon residue, for example.

While the foregoing is directed to embodiments of the present invention, other and further embodiments of the invention may be devised without departing from the basic scope thereof and the scope thereof is determined by the claims that follow.

We claim:

1. A method for the liquid-phase alkylation of an aromatic substrate comprising:
   providing an alkylation reaction zone having one or more catalyst beds, wherein the one or more catalyst beds comprises a first catalyst having a cerium ion modified zeolite beta catalyst for resistance to gas phase alkene deactivation by the inclusion of said cerium ion;
   introducing a feedstock of an aromatic substrate and an alkylating agent comprising ethylene into the alkylation reaction zone and into contact with the one or more catalyst beds wherein at least a portion of the ethylene is in a gas phase upon entering the alkylation reaction zone;

operating the alkylation reaction zone at temperature and pressure conditions in which the aromatic substrate is in a liquid phase to cause liquid-phase alkylation of the aromatic substrate to produce an alkylation product; and withdrawing the alkylation product from the multistage alkylation reaction zone;

wherein the one or more catalyst beds further comprise a second catalyst having a cerium content that is less than that of the first catalyst, and wherein the second catalyst is located downstream from the first catalyst within the one or more catalyst beds to thereby cause the first catalyst to contact the alkylating agent before the alkylating agent contacts the second catalyst;

wherein all of the ethylene is present in a liquid phase upon contacting the second catalyst.

2. The method of claim 1, wherein the first catalyst is located within the one or more catalyst beds to contact the alkylating agent prior to any other catalyst that may be present.

3. The method of claim 1, wherein the first catalyst has a cerium content within a range of about 0.01 wt % to 5.0 wt %.

4. The process of claim 1, wherein the first catalyst has greater resistance to gas phase ethylene than the second catalyst.

5. The method of claim 1 wherein the aromatic substrate comprises benzene and the alkylating agent comprises ethylene and the ethylene is provided from a dilute ethylene stream having less than 95% ethane content.

6. The method of claim 1 wherein the ethylene is provided from a dilute ethylene stream having less than 90% ethane content.

7. The method of claim 1 wherein the ethylene is provided from a dilute ethylene stream having less than 85% ethane content.

8. The method of claim 1 wherein the ethylene is provided from a dilute ethylene stream having less than 80% ethane content.

9. The method of claim 1 wherein the ethylene is provided from a dilute ethylene stream having an ethane content between 20% and 80%.

10. The process of claim 1, wherein the alkylation product from the alkylation reaction zone is supplied to an intermediate recovery zone for the separation and recovery of ethylbenzene from the alkylation product and for the separation and recovery of polyalkylated aromatic components, at least a portion of the polyalkylated aromatic component being supplied to a transalkylation reaction zone and wherein benzene is supplied to the transalkylation reaction zone and the transalkylation reaction zone is operated under temperature and pressure conditions to cause disproportionation of the polyalkylated aromatic fraction to produce a disproportionation product having an enhanced ethylbenzene content and a reduced polyalkylated aromatic components content.

11. The process of claim 10, wherein the transalkylation zone contains a transalkylation catalyst, wherein a type of catalyst that is used for said first modified catalyst is utilized for the transalkylation zone, and wherein said transalkylation zone is operated under temperature and pressure conditions effective to maintain the feedstock in the liquid phase.

12. The process of claim 1, wherein the feedstock has a benzene:ethylene ratio weight ratio per catalyst bed within a range of about 1:1 to 100:1.

13. The process of claim 1, wherein the feedstock has a benzene:ethylene ratio weight ratio per catalyst bed within a range of about 2:1 to 75:1.

14. The process of claim 1, wherein the feedstock has a benzene:ethylene ratio weight ratio per catalyst bed within a range of about 5:1 to 20:1.

15. A method for the liquid-phase alkylation of benzene comprising:

providing a multi-stage alkylation reaction zone having a plurality of series-connected catalyst beds, wherein at least one catalyst bed contains a first alkylation zeolite beta catalyst that is a cerium modified zeolite with elevated resistance to gas phase ethylene as compared to a non-modified catalyst;

introducing a feedstock of benzene and ethylene in a benzene:ethylene ratio weight ratio per catalyst bed within a range of about 1:1 to 15:1 into the multistage alkylation reaction zone and into contact with said alkylation catalyst;

operating the alkylation multistage reaction zone at temperature and pressure conditions in which the benzene is in a liquid phase to cause liquid-phase alkylation of the benzene in the presence of the alkylation catalyst to produce an alkylation product comprising ethylbenzene and one or more polyalkylated aromatic components;

withdrawing the alkylation product from the multistage alkylation reaction zone; and supplying the alkylation product to a recovery zone for the separation and recovery of ethylbenzene from the alkylation product and for the separation and recovery of polyalkylated aromatic components;

wherein the at least one catalyst bed contains a second alkylation catalyst, wherein the first alkylation catalyst has greater resistance to gas phase ethylene than the second alkylation catalyst, and wherein any feedstock of ethylene contacts the first alkylation catalyst prior to contacting the second alkylation catalyst;

wherein all of the ethylene is present in a liquid phase upon contacting the secondalkylation catalyst.

16. The method of claim 15, further comprising:

supplying at least a portion of the polyalkylated aromatic component to a transalkylation reaction zone that contains a zeolite transalkylation catalyst;

supplying benzene to the transalkylation reaction zone; and wherein the transalkylation reaction zone operated under temperature and pressure conditions to cause disproportionation of the polyalkylated aromatic component to produce a disproportionation product having an enhanced ethylbenzene content and a reduced polyalkylated aromatic component content.

17. The method of claim 15, wherein the transalkylation zone is operated under temperature and pressure conditions effective to maintain the feedstock in the transalkylation zone in the liquid phase.

18. The method of claim 15, wherein the zeolite transalkylation catalyst is a cerium-modified zeolite catalyst.

19. The method of claim 15, wherein the first catalyst has a cerium content within a range of about 0.01 wt % to 5.0 wt %.

20. The process of claim 15, wherein the feedstock has a benzene:ethylene ratio weight ratio per catalyst bed of less than 10:1.

21. The process of claim 15, wherein the feedstock has a benzene:ethylene ratio weight ratio per catalyst bed ranging from 3:1 to 8:1.

22. The method of claim 15 wherein the ethylene is provided from a dilute ethylene stream having less than 95% ethane content.

23. The method of claim 15 wherein the ethylene is provided from a dilute ethylene stream having less than 90% ethane content.

24. The method of claim 15 wherein the ethylene is provided from a dilute ethylene stream having less than 85% ethane content.

25. The method of claim 15 wherein the ethylene is provided from a dilute ethylene stream having less than 80% ethane content.

26. The method of claim 15 wherein the ethylene is provided from a dilute ethylene stream having an ethane content between 20% and 80%.

27. A method for the liquid-phase alkylation of an aromatic substrate comprising:

providing an alkylation reaction zone having one or more catalyst beds, wherein the one or more catalyst beds comprises a first catalyst having a cerium ion modified zeolite beta catalyst for resistance to gas phase alkene deactivation by the inclusion of said cerium ion;

introducing a feedstock of an aromatic substrate and an alkylating agent comprising ethylene into the alkylation reaction zone and into contact with the one or more catalyst beds wherein at least a portion of the ethylene is in a gas phase upon contacting the first catalyst;

operating the alkylation reaction zone at temperature and pressure conditions in which the aromatic substrate is in a liquid phase to cause liquid-phase alkylation of the aromatic substrate to produce an alkylation product; and withdrawing the alkylation product from the multistage alkylation reaction zone;

wherein the first catalyst has a cerium content within a range of about 0.01 wt % to 5.0 wt %;

wherein the one or more catalyst beds further comprise a second catalyst having no cerium content, and wherein the second catalyst is located downstream from the first catalyst within the one or more catalyst beds to thereby cause the first catalyst to contact the alkylating agent before the alkylating agent contacts the second catalyst;

wherein all of the ethylene is present in a liquid phase upon contacting the second catalyst.

* * * * *